US007604138B2

(12) United States Patent
Seher et al.

(10) Patent No.: US 7,604,138 B2
(45) Date of Patent: Oct. 20, 2009

(54) CLOSURE DEVICE FOR A CONTAINER

(75) Inventors: Jens-Peter Seher, Stuttgart (DE); Christopher Sprague Boit, Wellesley, MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 517 days.

(21) Appl. No.: 10/567,978

(22) PCT Filed: Aug. 3, 2004

(86) PCT No.: PCT/IB2004/051377

§ 371 (c)(1), (2), (4) Date: Feb. 10, 2006

(87) PCT Pub. No.: WO2005/013883

PCT Pub. Date: Feb. 17, 2005

(65) Prior Publication Data

US 2007/0023430 A1 Feb. 1, 2007

(30) Foreign Application Priority Data

Aug. 12, 2003 (EP) ................................ 03102509

(51) Int. Cl.

*B65D 39/00* (2006.01)
*B65D 41/00* (2006.01)
*B65D 43/00* (2006.01)
*B65D 47/00* (2006.01)
*B65D 51/00* (2006.01)
*A61B 69/00* (2006.01)
*B01L 11/00* (2006.01)

(52) U.S. Cl. ...................... 215/247; 604/403; 604/415; 422/103

(58) Field of Classification Search ................ 604/406, 604/408, 415; 422/102; 141/329; 436/180; 215/247

See application file for complete search history.

(56) References Cited

U.S. PATENT DOCUMENTS

| | | | | | |
|---|---|---|---|---|---|
| 4,134,512 | A | * | 1/1979 | Nugent | 215/247 |
| 4,935,010 | A | * | 6/1990 | Cox et al. | 604/122 |
| 5,169,602 | A | | 12/1992 | Pang et al. | 422/103 |
| 5,360,423 | A | | 11/1994 | McCormick | 604/403 |
| 5,425,465 | A | * | 6/1995 | Healy | 215/355 |
| 5,534,228 | A | * | 7/1996 | Wesseler | 422/103 |
| 5,945,070 | A | * | 8/1999 | Kath et al. | 422/101 |

(Continued)

FOREIGN PATENT DOCUMENTS

EP 0 398 321 A2 11/1990

(Continued)

*Primary Examiner*—Tatyana Zalukaeva
*Assistant Examiner*—Susan Su

(57) ABSTRACT

A closure device (10) for a container (12) includes a filling device (14) that can be attached to an opening (16) of the container (12) A closure structure such as a membrane (18), a system (34), or a duckbill closure (54, 84) is attached to the filling device (14) in such a way that the opening (16) of the container (12) is sealed when the filling device (14) is attached to the opening (16). The closure structure is coated at least partially with polytetrafluoroethylene (22, 38, 60, 94) on one side (20, 40, 58, 90) that is accessible from outside the container (12) in the assembled state of the filling device (14) on the container (12).

11 Claims, 2 Drawing Sheets

U.S. PATENT DOCUMENTS

| | | | | |
|---|---|---|---|---|
| 5,971,181 | A | 10/1999 | Niedospial et al. | 215/247 |
| 6,001,087 | A * | 12/1999 | Zurcher | 604/411 |
| 6,039,718 | A | 3/2000 | Niedospial | 604/408 |
| 6,171,287 | B1 | 1/2001 | Lynn et al. | 604/256 |
| 6,306,103 | B1 | 10/2001 | Tyler | 600/573 |
| 6,699,677 | B1 * | 3/2004 | Schall et al. | 435/7.24 |
| 6,715,624 | B2 * | 4/2004 | Brockwell | 215/247 |
| 7,163,114 | B2 * | 1/2007 | Okiyama | 215/247 |
| 2002/0130100 | A1 * | 9/2002 | Smith | 215/247 |
| 2002/0168530 | A1 * | 11/2002 | Tingey et al. | 428/421 |
| 2008/0015465 | A1 * | 1/2008 | Scuderi | 600/563 |

FOREIGN PATENT DOCUMENTS

| | | | |
|---|---|---|---|
| EP | 0 914 813 | A2 | 5/1999 |
| EP | 1 029 526 | A1 | 8/2000 |
| GB | 2 052 992 | A | 2/1981 |
| WO | WO 95/33505 | A1 | 12/1995 |

* cited by examiner

CLOSURE DEVICE FOR A CONTAINER

The invention relates to a closure device for a container.

In the medical sector, so-called point of care testing (POCT) has become ever more widespread in recent years. POCT is understood as meaning the testing and the analysis of biological material at the point of care or, in other words, in situ, such as, for example, in a hospital at a patient's bed. Whereas blood samples were previously taken from a patient and sent to a laboratory for analysis, it is nowadays possible by means of POCT to analyze and assess such a blood sample by means of a POCT analysis device in the vicinity of the patient, for example in the hospital ward that is caring for the patient. This can substantially accelerate the analysis and assessment of the blood sample. Automatic analytical means that comprise computer-controlled sensor systems for analyzing a biological material fed in are increasingly used for analysis and assessment.

In everyday clinical practice, POCT systems are preferably used to analyze and assess body fluids, such as, for example, blood samples. For this purpose, a sample of a body fluid to be analyzed is introduced into a container that is in turn inserted into an analytical or assessment device. The analytical or assessment device can then remove certain amounts of the sample contained in the container from the container for analysis and assessment.

In the field of POCT blood analysis, a patient's blood samples can be directly analyzed in situ by means of such containers. Typically, the containers provided for this purpose have special devices for receiving the blood to be analyzed. In this connection, the manufacturers of such containers use various configurations of the containers and the receiving devices for a blood sample. For example, some manufacturers use paper filters for receiving blood, whereas others use a Luer closure or a closable sample inlet seal.

Common to almost all configurations of containers is, however, the fact that the filling of a blood sample into a receiving device is not without danger for a user since, in the known containers, blood can rapidly spatter over the container or, still worse, over the user, for example, if the user does not find the inlet opening of the container precisely with the needle tip of the injection needle containing a blood sample. This frequently occurs, in particular, in the case of containers in which only a very narrow filling opening is provided, for example, for blood samples.

Various solutions are disclosed in the prior art that are intended, in particular, to facilitate the guiding of an injection-needle tip when filling a sample of a body fluid into a container. For example, U.S. Pat. No. 6,039,718 discloses a universal connector having a type of needle guide and integrated membrane that can be pierced by an injection-needle tip or a Luer syringe.

It is therefore an object of the present invention to propose a closure device for a container that improves the needle-guiding device or closure device for containers disclosed in U.S. Pat. No. 6,039,718.

The invention relates to a closure device for a container that comprises the following:

a filling device that can be attached to an opening of the container and a closure means that is attached to the filling device in such a way that the opening of the medical container is sealed when the filling device is attached to the opening and which closure means is coated at least partially with polytetrafluoroethylene on one side that is accessible from the outside of the container in the assembled state of the filling device on the container.

The closure device can preferably be pierced with a sharp object, in particular with an injection-needle tip. As a result, a sample can be introduced into the container without removing the closure means of the container. Preferably, the closure means is formed in such a way that it can be sealed again, that is to say, for example because of its elastic properties, the closure means re-forms again, in particular, at the pierced point when the sharp object that has pierced the closure means is removed again. In this connection, the re-formation should take place in such a way that the pierced point is sealed so that no fluid can reach the outside from the interior of the container through the closure means. As already indicated above, the sealing is substantially improved by coating the closure means with polytetrafluoroethylene.

Preferably, the closure means is a membrane. However, it may also be a septum. In a preferred embodiment, the closure means is a "duck-bill" valve device. In principle, such a valve device can be repeatedly used again, whereas a membrane or a septum must be replaced after a certain time of use, in particular after it has been pierced several times, in order to continue to seal the container in a fluid-tight manner.

The polytetrafluoroethylene coating can be formed on the closure means in such a way that it covers a region of the side of the closure means that is provided for piercing with a sharp object. As a result, it is unnecessary to coat the entire closure means or large regions of the closure means with polytetrafluoroethylene. In principle, it is sufficient if only a small region of the closure means is provided with the polytetrafluoroethylene coating. The remaining regions of the closure means should then be protected in such a way that they cannot be pierced by a sharp object that serves to introduce a sample into the container.

Preferably, the closure means itself is composed of silicone. Because of its properties, silicone proves to be particularly suitable for sealing a container and can easily be pierced by a sharp object, such as, for example, a needle tip.

In accordance with a particularly preferred embodiment, the closure means has a first region that comprises soft material having good adhesive properties. Furthermore, it comprises a second region that encloses the first region and comprises hard material. In the case of this structure, the first region is preferably coated with polytetrafluoroethylene and is provided for piercing. On the other hand, the second region serves as a type of suspension for the first region and cannot be pierced because of its hardness. Preferably, the second region, preferably the hard material of the second region, can be formed in such a way that it has resilient properties. Said resilient properties prove advantageous when the membrane is pierced by a needle tip since the first region yields when pressure is applied by the needle. The yielding forms a kind of guiding depression for the needle tip, which reduces the danger of the needle tip slipping off the membrane, in particular if the needle tip strikes the closure means at an unfavorable angle.

The filling device may have a Luer closure device that can be attached to the opening of the container. Such a closure device makes possible a simple and easily manipulated attachment of the closure device to the container.

In order to facilitate the filling of body fluid into the container through the closure device, the closure device has, in a preferred embodiment, a collecting space for receiving a sample of a biological material, such as, for example, a body fluid, that can be introduced into the collecting space through the closure means. The collecting space serves, so to speak, as a buffer space so that a more rapid filling of fluid into the container is made possible. Typically, a body fluid sample can be introduced, for example, by an injection syringe by means of an injection needle into the collecting space of the closure device in order then to flow from said collecting space into the container through the opening.

Finally, the invention relates to the use of a closure device in accordance with the invention in a preferably automatic analytical device for body fluids. An important idea of the invention is therefore that a closure means of the closure device has a coating containing polytetrafluoroethylene. Polytetrafluoroethylene, also known under the trade name of Teflon, has advantageous properties, in particular for use in the medical sector, such as resistance to almost all chemicals, temperature resistance and low wettability. Polytetrafluoroethylene also improves the sealing action of the closure means, in particular after it has been pierced by an injection-needle tip. Finally, polytetrafluoroethylene has good anti-friction properties so that, for example, an injection-needle tip can pierce the closure means particularly well. The manipulation of a closure device that is formed in accordance with the invention is therefore substantially simplified, particularly in everyday clinical practice.

These and other aspects of the invention are apparent from and will be elucidated with reference to the embodiments described hereinafter.

Figure 1:
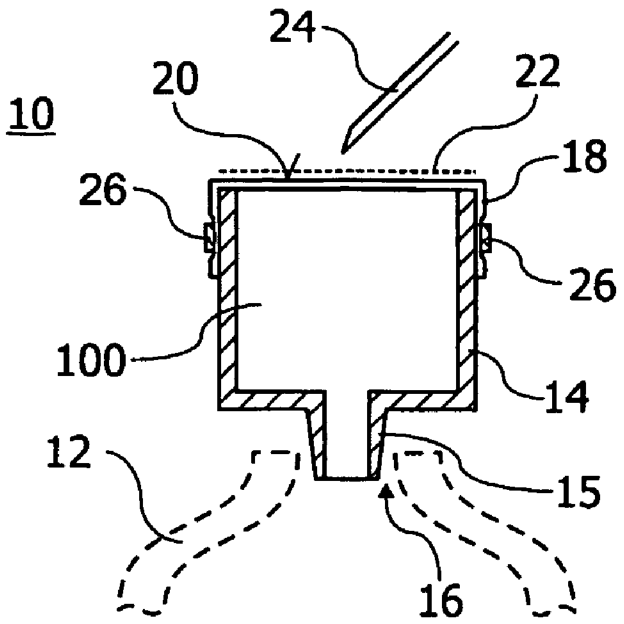
FIG. 1 shows a first exemplary embodiment of a closure device in accordance with the invention.

The closure device 10 shown in FIG. 1 serves to fill a container 12 shown by dotted lines, in particular a small tube for body fluids that can be introduced into an analytical means for body fluids.

The closure device 10 comprises a filling device 14 that has, in cross section, roughly the shape of a beaker. The filling device 14 comprises a Luer closure device 15 that is introduced into an opening 16 of the container 12 and is thereby attached to the container 12. Furthermore, the filling device 14 opens a collecting space 100 for receiving a body fluid introduced into the filling device 14.

The collecting space 100 of the filling device 14 is opened by the Luer closure device 15 so that a body fluid it contains can flow into the container 12 through the Luer closure device 15. The collecting space 100 is furthermore sealed in a fluid-tight manner on one side by a membrane 18. The membrane 18 is composed of silicone.

The outer side of the membrane 18, that is to say that side 20 of the membrane 18 that is remote from the collecting space 100, is provided with a polytetrafluoroethylene coating 22. To introduce the body fluid, an injection-needle tip 24 pierces the polytetrafluoroethylene coating 22 and the membrane 20. After the injection-needle tip 24 is withdrawn from the membrane 18 and the coating 22, the membrane 18, which is composed of silicone, automatically seals in a fluid-tight manner because of the polytetrafluoroethylene coating 22 and its elastic properties. As a result, the body fluid contained in the collecting space can no longer escape to the outside through the membrane 12, but can only flow into the container 12 through the Luer closure device 15.

The membrane is fixed on the filling device 14 by a ring fastener 26 that is composed, for example, of an elastic polymeric material. The ring fastener 26 makes possible an easy replacement of the membrane 18, for example if the membrane has already been pierced very often and has to be replaced for the closure device 10 to be used again.

Because of the low wettability of the polytetrafluoroethylene coating 22, if the injection-needle tip 24 slides off the membrane, there is little danger that body fluid escaping from the injection-needle tip 24 is spattered over the entire device 10. In the pierced state of the membrane 18, the coating 22 has, in addition, the effect that the injection-needle tip 24 slides easily and, because of its sealing properties, effectively prevents body fluid flowing through the injection-needle tip 24 into the collecting space 100 from being able to escape from the collecting space 100 at the pierced point 18 of the membrane. Finally, the coating 22 has the effect that, after the injection-needle tip 24 is removed from the membrane 18, the automatic sealing of the membrane 18 is improved.

Figure 2:
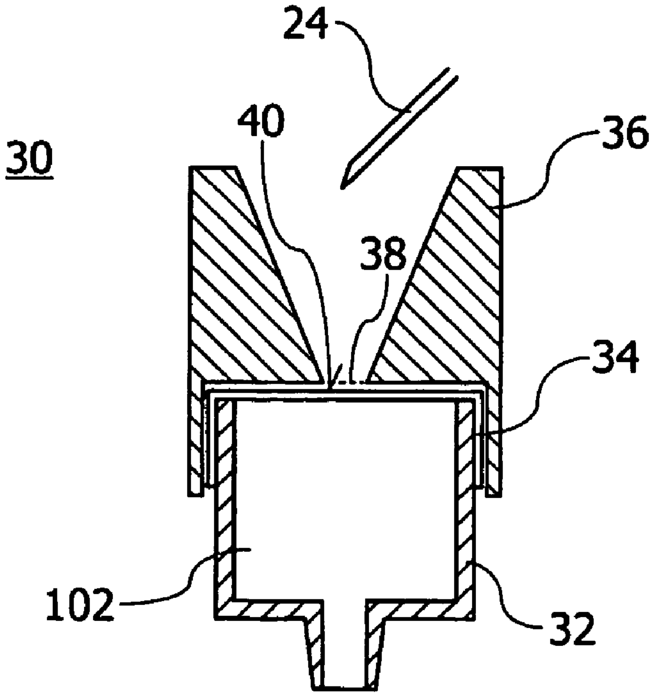
FIG. 2 shows a second exemplary embodiment of a closure device in accordance with the invention having a needle-guiding device.

FIG. 2 shows a closure device 30 that resembles the closure device 10 of FIG. 1, but has a septum 34 as closure means for the collecting space 102 of a filling device 32 of the closure device 30 instead of the membrane 18. The septum 34 is fixed to the filling device 32 by means of a needle-guiding device 36. For this purpose, the needle-guiding device 36 is partially pushed over the filling device 32 in such a way that the septum 34 is clamped between a part of the needle-guiding device 36 and the outer wall of the filling device 32.

Likewise in contrast to the closure device 10 shown in FIG. 1, the septum 34 has a smaller area that is provided with a polytetrafluoroethylene coating 38 on its outer side 40, that is to say on its side remote from the collecting space 102. Said smaller coated region of the outer side 40 of the septum 34 is necessary because the needle-guiding device 36 guides an injection-needle tip 24 for piercing the septum 34 to said region. As is shown in FIG. 2, the needle-guiding device 36 has a funnel-shaped cross section for this purpose. Because of said funnel-shaped cross section, the opening for introducing a needle tip to pierce the septum 34 is about as large as that area of the membrane 18 of the closure device 10 of FIG. 1 that is available for the piercing. Despite the needle-guiding device 36 used in the closure device 30, this closure device can therefore be manipulated conveniently, just like the closure device 10 of FIG. 1.

Figure 3:
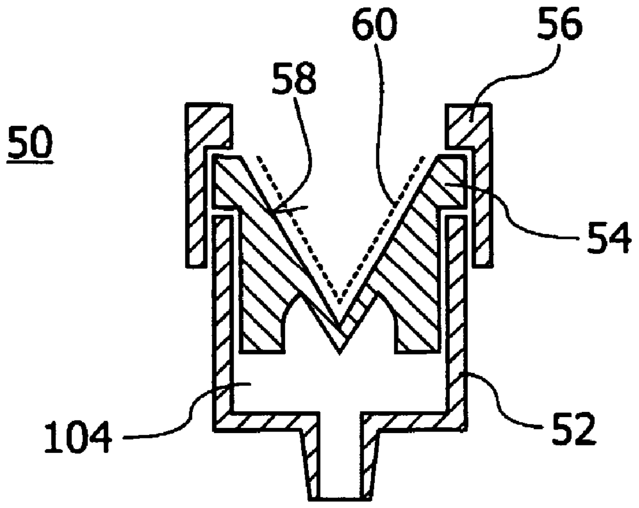
FIG. 3 shows a third exemplary embodiment of a closure device in accordance with the invention having a "duck-bill" valve device.

FIG. 3 shows a closure device 50 that, in contrast to the closure devices 10 and 30 of FIGS. 1 and 2, does not have a membrane and a septum for piercing, but has a "duck-bill" closure device 54 (duck-bill valve). Said "duck-bill" closure device 54 is provided on its outer side 58, that is to say the side remote from a collection space 104 of the closure device 50, with a polytetrafluoroethylene coating 60. The coating 60 almost completely covers the outward-facing region of the "duck-bill" valve device 54. The "duck-bill" valve device 54 is clamped by means of a ring fastening 56 on a filling device 52 of the closure device 50. Other joints between ring fastening 56 and filling device 52, for example a screw joint or a snap joint, are of course conceivable. The ring fastening 56 should be capable of being released again from the filling device 52 in order to be able to replace the "duck-bill" valve device 54.

Figure 4:
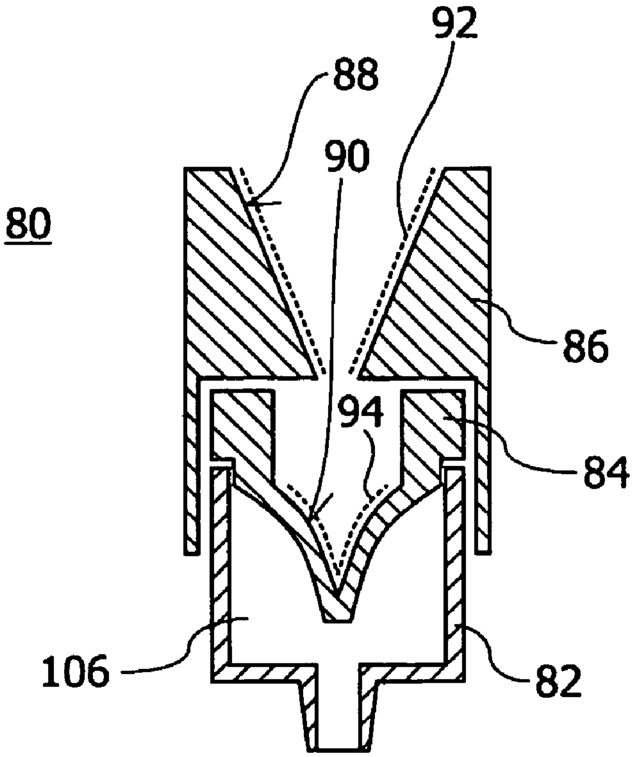
FIG. 4 shows a fourth exemplary embodiment of a closure device in accordance with the invention having a needle-guiding device and a "duck-bill" valve device.

Finally, FIG. 4 shows a further closure device 80 in accordance with the invention that likewise has a "duck-bill" valve device 84. In contrast to the closure device 50 shown in FIG. 3, in the case of said closure device 80, the "duck-bill" valve device 84 is mounted in a clamping fashion on a filling device 82 of the closure device 80 by means of a needle-guiding device 86. The needle-guiding device 86 has a polytetrafluoroethylene coating 92 on its outer side 88, that is to say that side of the needle-guiding device 86 that is accessible, for example, for an injection-needle tip. The "duck-bill" valve device 84 likewise has a polytetrafluoroethylene coating 94 on its outer side 90. Because of the design of the needle-guiding device 86, however, it is not necessary for the entire outer side 90 of the "duck-bill" valve device to be provided with the polytetrafluoroethylene coating 94. On the contrary, it is sufficient if only that region of the outer side 90 of the "duck-bill" valve device that is accessible for an injection-needle tip because of the needle-guiding device 86 is provided with the polytetrafluoroethylene coating 94. The polytetrafluoroethylene coating 92 of the needle-guiding device 86 is not absolutely necessary, but facilitates the manipulation of the closure device 80 since the injection-needle tip can then slide particularly well over the polytetrafluoroethylene coating 92 of the needle-guiding device 86.

This disclosure refers to preferred embodiments. Modifications and alterations may occur to others upon reading and understanding the preceding detailed description. It is intended that this disclosure be construed as including all such modifications and alterations insofar as they come within the scope of the appended claims or the equivalents thereof

LIST OF REFERENCE SYMBOLS

10 First closure device
12 Clinical container
14 Filling device
15 Luer closure device
16 Opening of the clinical container
18 Membrane
20 Outer side of the membrane
22 Polytetrafluoroethylene coating
24 Injection-needle tip
26 Ring fastening
30 Second closure device
32 Filling device
34 Septum
36 Needle-guiding device
38 Polytetrafluoroethylene coating
40 Outer side of the septum
50 Third closure device
52 Filling device
54 "Duck-bill" valve device
56 Fastening ring
58 Outer side of the "duck-bill" valve device
60 Polytetrafluoroethylene coating
80 Fourth closure device
82 Filling device
84 "Duck-bill" valve device
86 Needle-guiding device
88 Polytetrafluoroethylene coating
90 Polytetrafluoroethylene coating
92 Outer side of the needle-guiding device
94 Outer side of the "duck-bill" valve device

The invention claimed is:

1. A closure device for a container, comprising:

a filling device that can be attached to an opening of the container;

a closure means that is attached to the filling device in such a way that the opening of the container is sealed if the filling device is attached to the opening and which closure means is at least partially coated with polytetrafluoroethylene on one side that is accessible from outside the container in the assembled state of the filling device on the container, the closure means comprising:

a closure structure formed of soft material having good adhesive properties; and a needle guide that encloses the closure structure and a portion of a needle tip receiving side of the closure structure, the needle guide being formed of a hard material, the needle guide defining a funnel-shaped opening which directs the needle tip toward the closure structure;

a collecting space below the closure structure for receiving a fluid that can be introduced into the collecting space through the closure means.

2. The closure device as claimed in claim 1, wherein the closure means is a "duck-bill" valve device.

3. The closure device as claimed in claim 1, wherein the polytetrafluoroethylene is coated on the funnel-shaped surface.

4. A closure device which closes an opening of a point of care testing container which receives bodily fluids via a needle and which testing container is configured to be received in a point of care testing device, the closure device comprising:

a structure which defined a collecting space for receiving the bodily fluid;

a connecting structure which extends from the collecting space defining structure, the connecting structure being configured to connect with the opening of the point of care testing container;

a closure structure which closes an end of the collecting space opposite to the connecting structure, the closure structure being located above the collecting space and configured to be penetrated by the needle to introduce fluid into the collecting space and to seal when the needle is withdrawn;

a low wettability coating on at least a portion of the closure structure which inhibits body fluid which escapes fro the needle tip from spattering on the device and inhibits the body fluid from escaping from the collection space.

5. The closure device as claimed in claim 4, wherein the coating is polytetrafluoroethylene.

6. A closure device comprising:

a structure that defines a fluid collecting space;

a connecting structure that extends from and defines an outlet to the fluid collecting space, the connecting structure being configured to be connected to an opening of a container such that fluid drains from the collecting space into the container;

a closure structure which closes an end of the fluid collecting space opposite to the connecting structure, wherein the closure structure is located above the fluid collecting space;

a polytetrafluoroethylene coating on at least a portion of the surface of the closure structure opposite to the fluid collecting space;

wherein the closure structure and the polytetrafluoroethylene coating are configured to be penetrated by a tip of a needle which delivers the fluid into the fluid collecting space through the closure structure and the polytetrafluoroethylene coating and to seal against the fluid leaving the fluid collecting space

7. The closure device as claimed in claim 6, further including:

a needle guide disposed on a side of the closure structure opposite to the fluid collecting space, the needle guide defining a tapered passage which guides the needle to the polytetrafluoroethylene coated portion of the closure structure.

8. The closure device as claimed in claim 6, wherein the closure structure has a cross-section which is larger than a cross-section of the connecting structure such that it is easier to insert the needle into the closure structure than into the opening of the container.

9. The closure device as claimed in claim 6, wherein the closure structure includes:

a silicon membrane with the polytetrafluoroethylene coating on one surface.

10. The closure device as claimed in claim 6, further including:

a container connected to the connecting structure such that the fluid received in the fluid collecting space drains into the container.

11. The closure device as claimed in claim 10, wherein the fluids are bodily fluids and the container is a point of care testing container that is configured to be received in a point of care testing system which analyzes the bodily fluids at a point of patient care.

* * * * *